United States Patent
Chan et al.

(10) Patent No.: US 10,925,567 B2
(45) Date of Patent: Feb. 23, 2021

(54) ADAPTIVE IMAGING AND FRAME RATE OPTIMIZING BASED ON REAL-TIME SHAPE SENSING OF MEDICAL INSTRUMENTS

(75) Inventors: Raymond Chan, San Diego, CA (US); Jinnan Wang, Seattle, WA (US); Adrien Emmanuel Desjardins, Waterloo (CA); Luis Felipe Gutierrez, Jersey City, NJ (US); Maya Ella Barley, Walton on Thames (GB); Gert Wim 'T Hooft, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 413 days.

(21) Appl. No.: 13/881,179

(22) PCT Filed: Oct. 24, 2011

(86) PCT No.: PCT/IB2011/054728
§ 371 (c)(1),
(2), (4) Date: May 8, 2013

(87) PCT Pub. No.: WO2012/056386
PCT Pub. Date: May 3, 2012

(65) Prior Publication Data
US 2013/0216025 A1    Aug. 22, 2013

Related U.S. Application Data

(60) Provisional application No. 61/407,034, filed on Oct. 27, 2010.

(51) Int. Cl.
*A61B 5/00* (2006.01)
*A61B 6/00* (2006.01)
(Continued)

(52) U.S. Cl.
CPC .............. *A61B 6/488* (2013.01); *A61B 5/066* (2013.01); *A61B 6/12* (2013.01); *A61B 6/486* (2013.01);
(Continued)

(58) Field of Classification Search
CPC ......... A61B 6/488; A61B 34/20; A61B 5/066; A61B 6/486; A61B 6/54; A61B 6/542;
(Continued)

(56) References Cited

U.S. PATENT DOCUMENTS 5,255,680 A  10/1993  Darrow et al.
6,666,579 B2  12/2003  Jensen
(Continued)

FOREIGN PATENT DOCUMENTS

| JP | 06070457 | 11/1994 |
| JP | 2009279344 A | 12/2009 |
| WO | WO2005115058 | 12/2005 |
| WO | 2010065786 | 6/2010 |

OTHER PUBLICATIONS

D. Rand et al., "Issues, Models and Solutions for Triac Modulated Phase Dimming of LED Lamps", IEEE 2007, pp. 1398-1404.

*Primary Examiner* — Bill Thomson
*Assistant Examiner* — Joel M Lamprecht (57) ABSTRACT

A system and method for adaptive imaging include a shape sensing system (115, 117) coupled to an interventional device (102) to measure spatial characteristics of the interventional device in a subject. An image module (130) is configured to receive the spatial characteristics and generate one or more control signals in accordance with the spatial characteristics. An imaging device (110) is configured to image the subject in accordance with the control signals.

24 Claims, 5 Drawing Sheets

(51) Int. Cl.
*A61B 6/12* (2006.01)
*A61B 5/06* (2006.01)
*A61B 34/20* (2016.01)
*A61B 5/055* (2006.01)
*A61B 6/03* (2006.01)
*A61B 17/00* (2006.01)

(52) U.S. Cl.
CPC ............... *A61B 6/54* (2013.01); *A61B 6/542* (2013.01); *A61B 34/20* (2016.02); *A61B 5/055* (2013.01); *A61B 6/03* (2013.01); *A61B 6/487* (2013.01); *A61B 6/504* (2013.01); *A61B 6/5229* (2013.01); *A61B 2017/00075* (2013.01); *A61B 2034/2051* (2016.02); *A61B 2034/2061* (2016.02)

(58) Field of Classification Search
CPC .............. A61B 6/12; A61B 2034/2061; A61B 2034/2051; A61B 6/487; A61B 6/5229; A61B 2017/00075; A61B 6/03; A61B 5/055; A61B 6/504
See application file for complete search history.

(56) References Cited

U.S. PATENT DOCUMENTS

| | | | |
|---|---|---|---|
| 7,894,877 B2 | 2/2011 | Lewin et al. | |
| 8,364,245 B2 | 1/2013 | Kruecker | |
| 2002/0085681 A1 | 7/2002 | Jensen | |
| 2006/0013523 A1 | 1/2006 | Childlers et al. | |
| 2006/0293592 A1 | 12/2006 | Jensen | |
| 2007/0182347 A1 | 8/2007 | Shteynberg et al. | |
| 2007/0274450 A1* | 11/2007 | Niessen | A61B 6/08 378/119 |
| 2008/0118023 A1 | 5/2008 | Besson | |
| 2008/0281189 A1* | 11/2008 | Komuro | A61B 5/06 600/424 |
| 2008/0304198 A1 | 12/2008 | Chrishima | |
| 2009/0046906 A1 | 2/2009 | Wohlgemuth et al. | |
| 2009/0088629 A1 | 4/2009 | Groszmann et al. | |
| 2009/0137952 A1* | 5/2009 | Ramamurthy | A61B 5/06 604/95.01 |
| 2010/0030063 A1* | 2/2010 | Lee | A61B 5/06 600/424 |
| 2013/0216025 A1 | 8/2013 | Chan et al. | |

* cited by examiner

ADAPTIVE IMAGING AND FRAME RATE OPTIMIZING BASED ON REAL-TIME SHAPE SENSING OF MEDICAL INSTRUMENTS

This disclosure relates to medical imaging, and more particularly to a diagnostic or interventional control system for optimization or adaptation of imaging characteristics, e.g. imaging view, acquisition frame rate, etc.

There are a wide range of medical procedures that involve the insertion of a device into the human body under X-ray guidance. These procedures include guiding catheters to perform vascular procedures such as stent placements, and needles to perform tissue biopsies and ablations. X-ray fluoroscopy can be of considerable importance in identifying anatomical landmarks at known positions relative to a target position for the device. With X-ray fluoroscopy, physicians can acquire a single image or multiple images in rapid succession (e.g., as a video).

With multiple images in rapid succession, there is a risk that the X-ray exposure to the physician and the patient is significantly greater than is necessary for the procedure to be performed effectively. This can result from the acquisition of images performed when: a) the device is not moved over a significant distance relative to the image resolution; and/or b) the device is moved predominantly in a direction perpendicular to the imaging plane and so little apparent movement of the device occurs within the projection image.

In both cases, the use of multiple X-ray images will likely not provide any useful clinical information, but it will expose the patient and the physician to higher X-ray doses. A patient undergoing a single procedure may not be at high risk for the deleterious effects of X-rays, but for physicians who perform many procedures each day, dose reduction is extremely important—and it is an issue that many physicians are highly conscious of. Decreasing X-ray exposure is particularly important with modalities such as cine-fluoroscopy, where higher doses are used relative to low-dose fluoroscopy.

During interventional procedures performed under X-ray fluoroscopic guidance, significantly more images than are necessary to effectively perform the procedures may be acquired. This results in an unnecessary increase in exposure of harmful X-rays to physicians and patients. In addition, during interventional procedures, imaging characteristics are typically updated manually by the clinical staff, e.g., to attempt to optimize X-ray gantry angulation, detector height, table location, etc. for optimal viewing of the interventional field and anatomy of interest. For magnetic resonance (MR) based procedures, scan plans are prescribed by an MR technologist working with the clinical team. These manual adjustments often lead to less than optimal clinical workflows and can result in less than optimal image quality.

In accordance with the present principles, a system and method for adaptive imaging include a shape sensing or localization system coupled to an interventional device to measure spatial characteristics of the interventional device or other target of interest in a subject. An image acquisition module is configured to receive the spatial characteristics and generate one or more control signals in accordance with the spatial characteristics. An imaging device is configured to image the subject in accordance with the control signals.

A workstation includes a processor and a memory coupled to the processor. The memory stores a shape sensing module and an image module. The shape sensing module is configured to determine spatial characteristics of an interventional device. The image module is configured to adjust an imaging device in accordance with the spatial characteristics to provide image collection settings useful for a given medical procedure.

A method, in accordance with the present principles, includes shape sensing an interventional device to measure spatial characteristics of the interventional device in a subject; generating one or more control signals in accordance with the spatial characteristics; and adjusting an imaging device to image the subject in accordance with the control signals.

These and other objects, features and advantages of the present disclosure will become apparent from the following detailed description of illustrative embodiments thereof, which is to be read in connection with the accompanying drawings.

This disclosure will present in detail the following description of preferred embodiments with reference to the following figures wherein.

The present principles provide systems and methods for real-time shape information derived from a medical device or other target tracked in vivo, e.g., with fiber-optic shape sensing or with an electromagnetic position and orientation measurement system or other similar localization platform. The shape information may be used to dynamically adapt a frame rate or other imaging characteristic or functionality of an imaging system, e.g., an X-ray (fluoroscopic) system. The frame rate is adapted, for example, to minimize X-ray exposure of physicians and patients, while providing accurate visualization of a device, e.g., in a minimally foreshortened view by automatic positioning of a gantry based on localization information derived from the tracked target. The frame rate may be adapted to trade off between temporal and spatial resolution in the case of magnetic resonance (MR) image acquisition and reconstruction. If the device has moved only a small distance since a previous fluoroscopy image was acquired, a new fluoroscopy image may not be acquired, but a marker indicating a new shape and/or location of the device may be overlaid on the previous fluoroscopy image.

Motion data measured from an instrument may represent a dominant change within an interventional workspace and may be used with prior imaging frame data to compute a new image with the instrument features correctly represented. A computed tomography (CT) system may be employed for instrument tracking instead of a fluoroscopy system. In an embodiment using magnetic resonance imaging (MRI), independently acquired information about instrument movement may be fed back into an MRI pulse sequence acquisition to automatically adapt sequences to increase scan signal to noise ratio (SNR) or spatial resolution during time intervals in which little change in instrument motion is present (and vice versa). For ultrasound, the probe may be automatically manipulated or configured to optimize the quality of the acquired ultrasound image of the localized target. Similarly, nuclear medicine imaging methods may use localization information from the target to optimize the positioning of the detectors for maximal SNR. The information for optimization may be coupled back in an automated feedback control loop, or may be displayed visually in a user interface for manual system configuration.

Real-time shape information (e.g., from fiber optic shape sensing or electromagnetic position and orientation sensing) for medical instrumentation tracked in-vivo is employed to dynamically adapt imaging system characteristics to ensure optimal visualization, device navigation, and intervention planning within a desired field-of-view. The present principles simplify imaging and improve data acquisition for multiple imaging modalities. For example, in one embodiment, in interventional X-ray systems, a tracked interventional device, such as a coronary guidewire inserted into the vascular system, provides live shape/position/orientation data about a tip segment and thus permits automated table adjustments (panning/height) or C-arm gantry angulations to keep the segment optimally visualized within the X-ray field-of-view. In one instance, these adjustments automatically ensure that the coronary vessel and guidewire are maintained in a minimally foreshortened view as a coronary intervention is being performed. Automated prescription of imaging system characteristics and streamlined clinical workflow are achieved while optimizing the quality of images acquired.

The elements depicted in the FIGS. may be implemented in various combinations of hardware and provide functions which may be combined in a single element or multiple elements. It should be understood that the present invention will be described in terms of medical instruments; however, the teachings of the present invention are much broader and are applicable to any instruments employed in tracking or analyzing complex biological or mechanical systems. In particular, the present principles are applicable to internal tracking procedures of biological systems, procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

With the advent of robust and real-time mechanisms for integrated localization of medical instruments within an interventional setting, e.g., with fiber shape sensing or next-generation electromagnetic tracking systems, information about the shape and/or location of a device to a processor is provided to automatically optimize the rate at which fluoroscopic images are acquired during interventions. Instrument tracking can be performed with optical fiber-based sensing of strains which can be integrated over a length for local shape estimation. Optical fiber-based measurements of geometry will be described in accordance with the present principles for at least the following reasons. Optical fiber-based measurements are immune to electromagnetic interference and require no electromagnetic emissions. Related sensors are passive and therefore intrinsically safe. The ability for multiplexing sensors exists in a sensor array. The possibility of multi-parameter sensing (strain, temperature, pressure, etc.) and distributed sensing is provided. The sensors have high sensitivity (e.g., down to nanostrains when interferometry is used in optical interrogation). Optical fibers are small, light-weight, ideal for minimally invasive applications, and insensitive to variation in signal amplitude (e.g., when fiber Bragg sensors are employed with wavelength detection).

Optical fiber-based shape sensing technology offers high-accuracy and high-precision localization at high spatio-temporal resolution along the length of the fiber. Given the light-weight, elongated form factor of optical fiber and its compact cross-sectional footprint, this fiber technology fits well within medical instrumentation of the present principles although other technologies may be employed. For example, tracking can also be performed with electromagnetic tracking (EM) systems which are robust in confounding conductive structures in the interventional environment.

In one embodiment, control of the rate at which images are acquired is provided by tracking the movement of the interventional device in real-time and acquiring images only when there is significant movement of the device in the imaging plane. This problem of automatic frame rate adjustment is inadequately addressed by imaging alone. If image processing were used to track the motion characteristics of a device, the frame rate could be reduced to match a slowly moving instrument. However, at a lower sampling rate, temporal aliasing could occur when the device begins moving more rapidly, leading to lag and misrepresentation of device motion until the acquisition frame rate is increased again. Independent motion tracking by optical fiber-based sensing or next-generation EM measurements may address these problems.

Optimal positioning of image acquisition scan planes and angulations is needed for accurate monitoring of interventional procedures. With the advent of robust and real-time mechanisms for integrated localization of medical instruments within an interventional setting such as with fiber shape sensing or next-generation electromagnetic tracking systems, measured tracking data is coupled in a feedback control loop with an image acquisition system to permit automated manipulation of imaging system characteristics to optimize scanning during interventions. Next generation instrument tracking can be performed with optical fiber-based sensing of strains which can be integrated over a length for local shape estimation. Instrument shape and localization data can be streamed live to the imaging system console for automation and/or optimization of scan characteristics.

Figure 1:
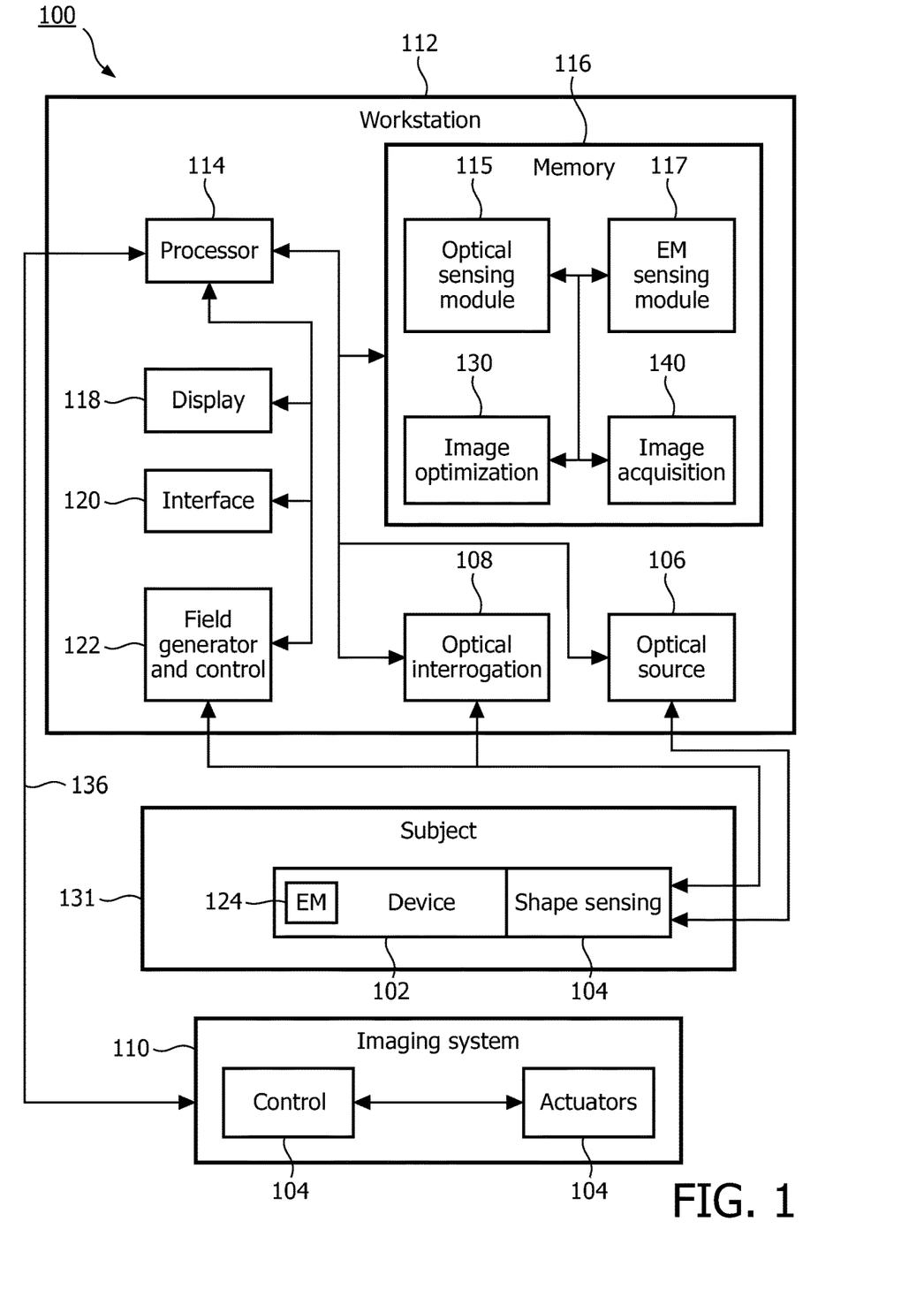
FIG. 1 is a block/flow diagram showing a system for adaptive imaging in accordance with one illustrative embodiment.

Referring now to the drawings in which like numerals represent the same or similar elements and initially to FIG. 1, an adaptive imaging system 100 responsive to interventional instrument feedback is illustratively shown. System 100 includes a tracked medical device or instrument 102 used during an interventional procedure within a subject 131. The instrument 102 may include a catheter, wire, needle or other interventional device. The instrument 102 may include a shape sensing or localization system 104. The shape sensing system 104 tracks instrument shape, position, and/or orientation measurements. The shape sensing system 104 may include a fiber optic shape sensing system (e.g., with Fiber Bragg Gratings or Rayleigh scatterers), an EM tracking system, or another tracking system.

If the fiber optic system is employed as the shape sensing system 104, an optical source 106 is employed for shape sensing fiber illumination. An optical interrogation unit 108 is employed to detect light returning from all fibers. This permits the determination of strains or other parameters, which will be used to interpret the shape, orientation, etc. of the interventional device 102. The light signals will be employed as feedback to make adjustments to other systems, such as imaging systems 110.

System 100 may include a workstation or console 112, which provides a plurality of tools and functions for carrying out a procedure in accordance with the present principles. The workstation or console 112 may provide surgical tools, controls, power sources, interfaces etc. In a particularly useful embodiment, workstation 112 includes a processor 114, memory 116, a display 118 and a user interface 120. The processor 114 implements a real-time optical sensing module 115 for sensing fiber shape, position, orientation of the fiber bundles.

In an alternate embodiment, the shape sensing system 104 employs electromagnetic (EM) tracking. In this embodiment, an electromagnetic (EM) field generator and control unit 122 are employed. An EM coil(s) 124 is/are embedded within the tracked medical instrument 102 at a plurality of locations. It should be understood that EM tracking and fiber optic shape sensing may be employed separately or together. Other shape sensing devices and systems may also be employed. The processor 114 implements a real-time EM tracking and sensing module 117 for sensing shape, position, orientation of the interventional instruments 102. The processor 114 and modules 115 and/or 117 sense instrument shape, position, and orientation using optical and/or EM tracking signals (e.g., EM field distortion compensation). Alternative tracking systems based on other physical principles, e.g. acoustic, infrared, imaging and image processing, etc. may also be employed with the tracked elements that can be incorporated into medical instruments and used in vivo.

The imaging system 110 is employed for monitoring a procedure, guidance of an intervention, etc. Imaging system 110 may include a fluoroscopy system, a magnetic resonance system, a computed tomography system, etc. An imaging optimization program or module 130 is stored in memory 116 or may be stored in the imaging system 110. The imaging optimization program 130 implements real-time methods to derive optimal imaging system characteristics based on real-time instrument position, orientation, and shape information.

One or several programmable effectors/actuators 134 are responsive to signals sent from the processor 114 as determined by the imaging optimization program 130. The actuators 134 modify imaging system attributes or imaging system characteristics based on real-time instrument position, orientation, and shape information and feedback.

A data connection 136 is coupled to the processor 114 and carries control signals to an imaging system control unit 138. The control signals are generated based on interpretations of the instrument shape sensing system 104. Signals output by the shape sensing system 104 are interpreted by modules 115 and/or 117, and the results are applied to the imaging optimization program 130 which optimizes characteristics of the imaging system 110. The control unit 138 and actuators 134 are adjusted to alter the imaging device configuration to optimize image collection. For example, actuators 134 may adjust gantry angulation, MR scan prescription, exposure time, frame rate, etc. The shape sensing system 104 provides real-time shape, localization data or information derived from such data (e.g. scan planes perpendicular to the fiber-optic long-axis) to the processor 114 for automated adaptive control of the imaging system geometry or other imaging system attributes. This may include X-ray source exposure, frame rate, image icons or displays, video tools or other imaging system characteristics.

In one embodiment, X-ray guided interventions can be simplified by coupling X-ray system characteristics, e.g., table position, gantry angulation, etc., with the shape sensing or tracking system 104. Derived information from tracking system 104 is employed for optimal visualization of a tracked medical instrument, e.g., a tracked coronary guidewire or intravenous ultrasound (IVUS) catheter within an anatomy of interest is dynamically tracked by the X-ray detector in a "follow-me" mode that permits for visualization of the coronary with minimal foreshortening at any given moment.

Figure 2:
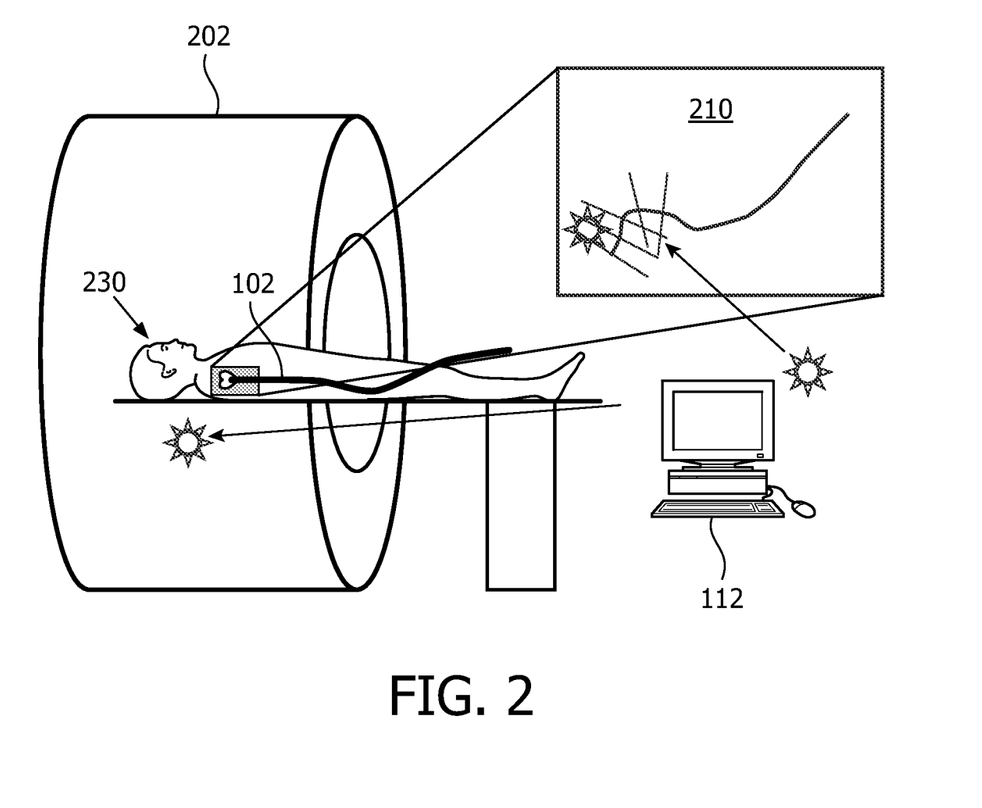
FIG. 2 is a diagram showing a magnetic resonance system with for adaptive imaging in the form of a modified prescriptive scan in accordance with one illustrative embodiment.

Referring to FIG. 2 with continued reference to FIG. 1, an MR embodiment is illustratively shown. Tracking in this case will be with fiber optic sensing (104) given that current generation electromagnetic tracking systems do not function accurately in the presence of an MR magnet in an MR scanner 202. External tracking is attractive since MR-based tracking needs additional interleaving of localization pulse sequences which represent additional acquisition and processing overhead. This reduces frame rates available for intervention guidance.

The tracked data, obtained from the instrument 102 being manipulated, are fed back automatically to workstation 112 which computes new scan prescriptions 210 based on the shape of the interventional instrument 102. The scan prescription(s) 210 focus imaging operations on a particular portion or region of interest of a patient 230. Possible scan prescriptions may include automated non-linear scanning along the instrument 102 (e.g., a coronary catheter or guidewire) long-axis, potentially for volumetric coronary imaging or automated "live" acquisition of interventional imaging planes that dynamically follow the instrument tip frame-of-reference. In other embodiments, scan prescriptions may involve additional resolution or view angles for a particular point of interest based upon feedback from the shape sensing system 104. For example, device 102 includes a catheter with a tip providing a reference frame. An automated scan prescription is determined, for example, for a non-rectilinear scan plane acquisition using the catheter tip as a reference point or for a live acquisition of interventional scan planes relative to the catheter tip position. Further benefits include automated scan prescriptions of non-linear trajectories when imaging anatomical structures which lie parallel to an axis of instrument 102, allowing for minimization of partial volume effects (e.g., vessel wall imaging with MRI when used in conjunction with a tracked coronary guidewire).

Referring again to FIG. 1, in the case where multiple instruments are tracked in a same procedure, the imaging optimization program 130 derives X-ray imaging characteristics that are optimal either for a) visualizing one of the tracked instruments (102), or b) visualizing two or more of the tracked instruments. The metrics used for optimization in case a) could differ from those used in case b). For example, in case b), the metrics may include optimizations for visualizing relationships between the positions of two or more of the tracked instruments.

The output of the shape determination modules 115 and/or 117 may include estimates of error associated with shape parameters of the tracked instrument(s) 102. In this case, the rate of change of the imaging characteristics could be made dependent on the magnitudes of those errors. For example, if the instrument shape changes quickly and large errors are involved in the shape measurement, the imaging system 110 would not respond (or would respond very slowly) until the errors had reduced significantly in magnitude.

In the case where multiple imaging systems 110 are used simultaneously for multimodality guidance (e.g., a combination of X-ray, ultrasound (US), CT, MR, etc.), the imaging optimization program 130 derives imaging characteristics that are optimal for visualization with one of the imaging systems 110, or with two or more of the imaging systems 110. The metrics used for optimization of one system could differ from those used in optimization of multiple imaging systems.

The present embodiments pertain to all imaging modalities for which scan parameters or system attributes need to be adjusted for intervention monitoring. Likewise, any clinical procedures performed under image guidance for which tracking data from the instruments used can further enhance imaging performance or clinical workflow.

Modules 115 and/or 117 sense the shape, position and orientation of the tracked instrument 102. Modules 115 and/or 117 implement real-time algorithms for instrument shape, position, and orientation measurements. An image acquisition program or module 140 is included to optimize a rate at which X-ray images are acquired based on the movement, position, orientation, etc. of the interventional device 102. Module 140 may be part of module 130 or may be a separate module (as depicted in FIG. 1). Data is provided between the shape sensing system 104 and the image acquisition module 140 so that information about the shape and location of the device 102 can be provided to the image acquisition module 140 in real-time to optimize a rate at which X-ray images are acquired. Image acquisition module 140 generates signals that are sent through data connection 136 to the control unit 138 of image system 110. The image acquisition rate is controlled in accordance with feedback from the position, motion and usage of the interventional device 102.

Figure 3:
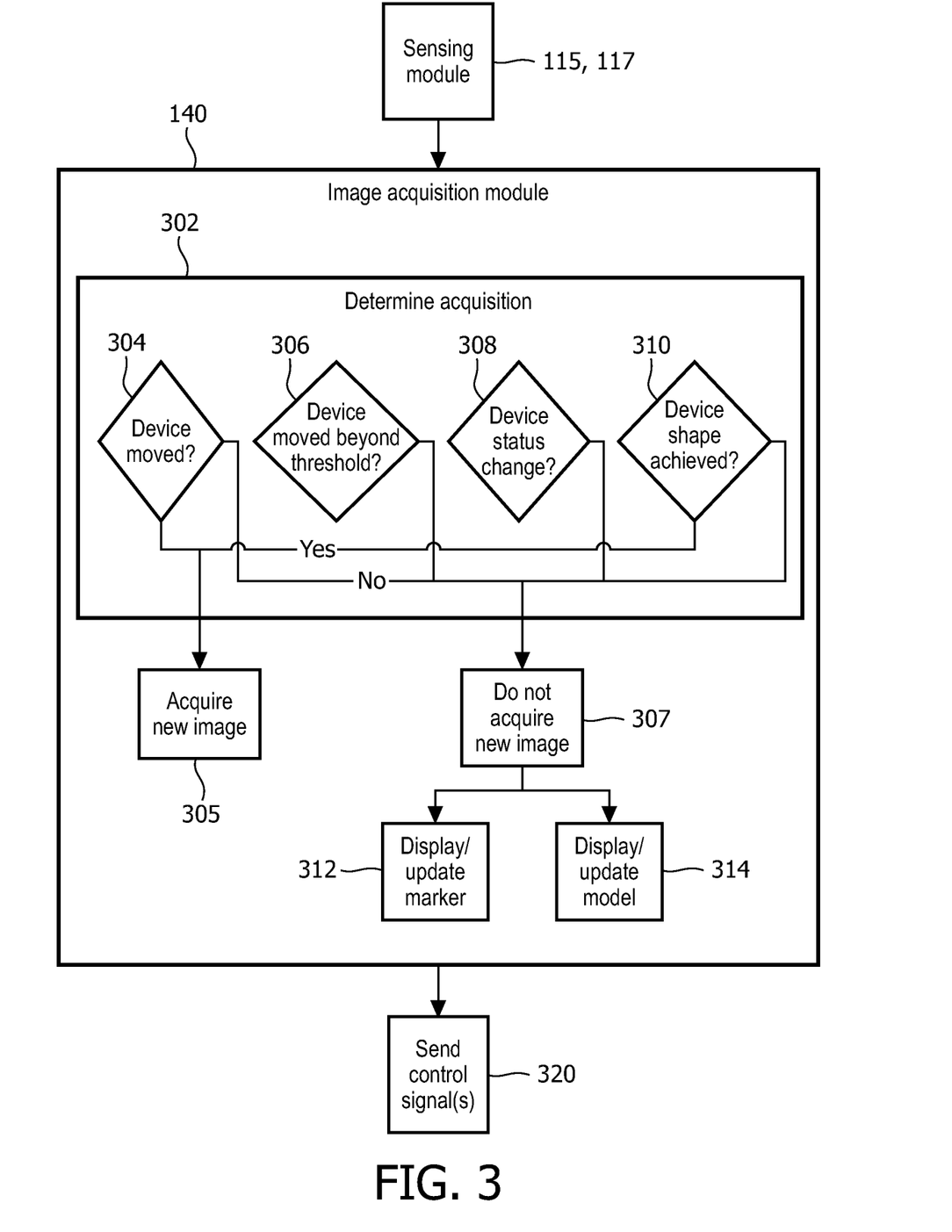
FIG. 3 is a block/flow diagram showing an image acquisition module for deciding whether to acquire a new image or not in accordance with one illustrative embodiment.

Referring to FIG. 3 with continued reference to FIG. 1, a block diagram shows a block/flow diagram for the image acquisition module 140 in accordance with one illustrative embodiment. The interventional device 102 provides shape sensing signals to modules 115 and/or 117 which derive information about the shape and/or location of the interventional device 102. In block 302, the image acquisition module 140 determines whether another fluoroscopy image (or other image) needs to be acquired. A determination is made based on different criteria, as to whether a new image should be acquired in block 305 or not in block 307. In one embodiment, the determination includes any movement of the interventional device in block 304. If the device moves then a new image is acquired. Real-time information about the shape and/or location of the interventional device 102 is derived independently of the image information provided by imaging system 110. In this embodiment, a binary decision is made by the image acquisition module 140. If the device moved significantly since the previous fluoroscopy image was acquired, a new fluoroscopy image is acquired. Otherwise, a fluoroscopy image is not acquired.

In another embodiment, an additional determination of how much the interventional device 102 has moved is made in block 306. If this movement exceeds a threshold then a new image is acquired. Otherwise, no new image is acquired. In yet another embodiment, a type of movement is determined in block 310. If the type of movement, e.g., a compound flexure, cumulative displacement, rotation, bend, etc., is achieved by the interventional device 102 then a new image is acquired. Otherwise, no new image is acquired. In yet another embodiment, the image acquisition or acquisition rate may be altered based upon the status, usage or functioning of the interventional device in block 308. For example, if the interventional device is an ablation device, acquisition rate may be altered upon commencement of ablation.

In one example, if the device 102 is moved only a small distance since the previous fluoroscopy image was acquired (with the definition of "small distance" defined based on the physician's preferences), a new fluoroscopy image is not acquired (block 307), but a marker indicating a new shape and/or location of the device 102 is overlaid on the previous fluoroscopy image in block 312.

Figure 4:
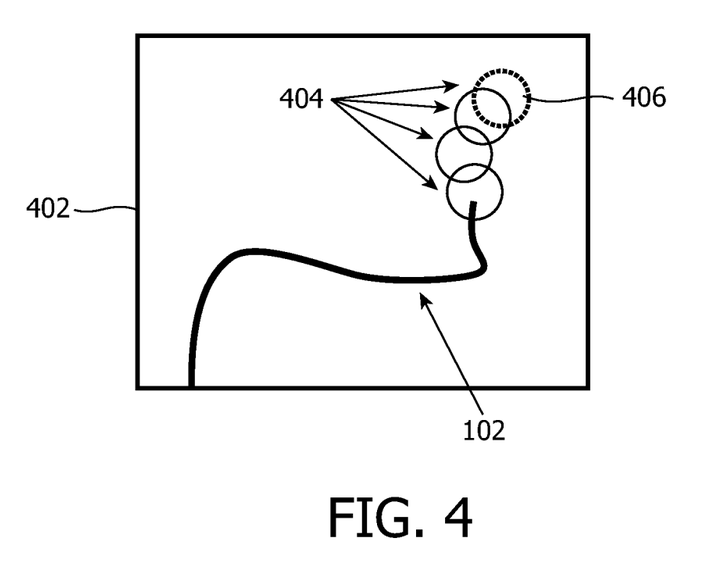
FIG. 4 is a block/flow diagram showing an image having a marker generated to replace the need for acquiring a new image in accordance with one illustrative embodiment.

Referring to FIG. 4, a diagram shows an example of a display 402 produced with markers 404 indicating a new shape and/or location of the device 102. The image of a flexible device (e.g., a catheter) 102 as acquired by fluoroscopy is overlaid with circles (markers 404) that indicate updates of the location of a device tip obtained from the shape sensing system 104. A dashed circle 406 indicates the most recent location of the device tip. The circles (404) are provided as updates to the display 402 without the acquisition of new fluoroscopy images. The diameter of the circle could indicate positional uncertainty (e.g., error). In this example display 402, only a tip location is shown, but other displays could be provided that indicate additional information obtained from the shape sensing system 104 (e.g., the shape of the device).

Referring again to FIG. 3, in block 314, another embodiment employs computational processing/modeling of image frames based on previous frames acquired, and a measured shape deformation of a medical instrument from optical fiber-based shape sensing or next generation EM tracking. Motion data measured from the instrument 102 represents a dominant change within the interventional workspace and can be used together with prior imaging frame data to compute a new image with the instrument features correctly represented within. This approach can be used to achieve high frame rate interpolation or extrapolation from low-frame rate (low-dose) X-ray (or CT) acquisitions. A model of the intervention device in the image is progressively moved to avoid the need for more image acquisitions. This can lower radiation exposure.

In another embodiment, a CT system (or other system) is employed for instrument tracking in place of a fluoroscopy system. With a CT system, X-ray exposure is generally much greater than that of a fluoroscopy system, so the problem of minimizing X-ray exposure could be more important.

In yet another embodiment, MR trades off SNR, spatial resolution, and temporal resolution. Using a tracked instrument 102 based on rapid optical fiber-shape sensing, temporal information about the change in image features during an intervention can be obtained without the overhead of MR tracking pulse sequences. The independently acquired information about instrument movement can be fed back into an MRI pulse sequence acquisition to automatically adapt sequences to increase scan SNR or spatial resolution during time intervals in which little change in instrument motion is present (and vice versa). This may result is less imaging time and/or improved resolution under particular conditions (e.g., low or no device movement).

After the image acquisition module 140 has determined whether to acquire a new image or not, an appropriate control signal or signals are generated and output to imaging devices (110) in block 320. The imaging device or devices are controlled to acquire new images or not accordingly.

Figure 5:
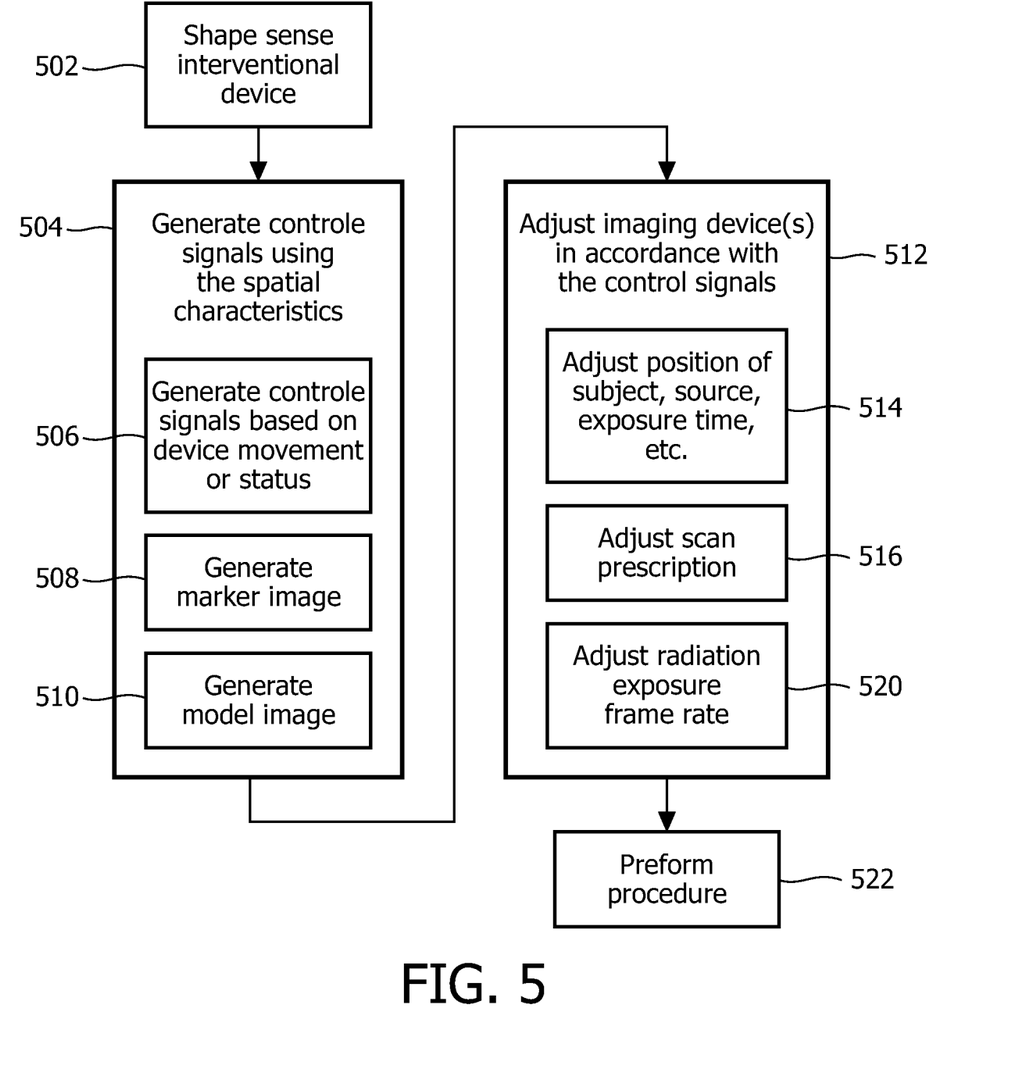
FIG. 5 is a flow diagram showing steps for adaptive imaging in accordance with an illustrative embodiment of the present invention.

Referring to FIG. 5, a block/flow diagram is shown depicting a system/method for adaptive imaging in accordance with the present principles. In block 502, shape sensing of an interventional device is performed to measure spatial characteristics of the interventional device in a subject. The shape sensing may include optical fiber-based sensing, electromagnetic sensing, another shape sensing method or combinations of these. In block 504, one or more control signals are generated in accordance with the spatial characteristics. The control signals are generated using the spatial characteristics provided by the shape sensing.

In one embodiment, in block 506, a control signal is generated to acquire an image based upon at least one of: movement of the interventional device, movement of the interventional device beyond a threshold amount and a type of motion of the interventional device. In block 508, a marker image may be generated in accordance with the spatial characteristics to indicate an updated position of the interventional device in a display. In block 510, a model image of the interventional device may be generated in accordance with the spatial characteristics to indicate an updated position of the interventional device in a display. Blocks 508 and 510 eliminate or reduce an image acquisition rate since the update of interventional device movement is performed artificially in a digital image.

In block 512, an imaging device or devices are adjusted to image the subject in accordance with the control signals. In this way, the shape, position, orientation, status, etc. of the interventional device are employed to determine the imaging device settings, configuration, exposure time/rate, pulse rate, etc. For example, the imaging device may include an X-ray exposure device (fluoroscopic device, computed tomography device, etc.). The imaging device may be adjusted by modifying a position of the subject, a position of an X-ray source, an exposure time, etc. in block 514. The imaging device may be guided in accordance with a scan prescription such that the scan prescription is modified in accordance with the spatial characteristics in block 516. This is particularly useful with MR scans. In block 520, the imaging device may be adjusted by controlling a radiation exposure frame rate of the imaging device using the control signals based upon the spatial characteristics. In block 522, an operational procedure is carried out using the adaptive feedback imaging as needed in accordance with the present principles.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function; and e) no specific sequence of acts is intended to be required unless specifically indicated.

Having described preferred embodiments for systems and methods for adaptive imaging and frame rate optimizing based on real-time shape sensing of medical instruments (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A system comprising:
    a processor;
    a shape sensor coupled to an interventional device and configured to measure shape sensing information comprising shapes and locations of the interventional device within a subject;
    a memory coupled to the processor and configured to store an imaging program that, when executed by the processor, receives the shape sensing information from the shape sensor, determines when to acquire images of the subject in response to an amount or type of movement of the interventional device indicated by the shape sensing information, and automatically initiates one or more control signals indicating when it is determined that images of the subject are to be acquired; and
    an imaging device configured to acquire the images of the subject in response to the one or more control signals.

2. The system as recited in claim 1, wherein the imaging device includes an X-ray exposure device having an X-ray source for acquiring the images of the subject, wherein the one or more control signals further control at least one of a position of the X-ray source and an exposure time for the acquired images of the subject.

3. The system as recited in claim 1, wherein it is determined that the images are to be acquired when the interventional device moves beyond a threshold amount.

4. The system as recited in claim 1, wherein the imaging program, when executed by the processor, further generates a model image of the interventional device in accordance with the shape sensing information, the model image being configured to indicate an updated position of the interventional device in a display without the imaging device acquiring another image.

5. The system as recited in claim 1, wherein the shape sensor is optical fiber-based or electromagnetic.

6. The system as recited in claim 1, wherein the memory further stores a scan prescription for acquiring images of the subject, and the scan prescription being modified in accordance with the shape sensing information.

7. The system as recited in claim 1, wherein the one or more control signals indicate adjusting a frame rate of the imaging device when it is determined that the images of the subject are to be acquired based upon the shape sensing information.

8. The system as recited in claim 1, wherein the imaging program, when executed by the processor, further generates a marker image in accordance with the shape sensing information, the marker image being configured to indicate an updated position of the interventional device in a display without the imaging device acquiring another image.

9. A workstation, comprising:
a processor; and
a memory coupled to the processor, and storing a shape sensing module that, when executed by the processor, determines shape sensing information comprising shapes and locations of an interventional device within a subject, and an image module that, when executed by the processor, receives the shape sensing information and determines when to control an imaging device to acquire images of the subject during a medical procedure based on an amount or type of movement of the interventional device indicated by the shape sensing information received from the shape sensing module.

10. The workstation as recited in claim 9, wherein the imaging device includes an X-ray exposure device and the workstation is configured to provide improved images by selecting a position of an X-ray source and an exposure time corresponding to the acquired images.

11. The workstation as recited in claim 9, wherein it is determined to acquire the images when the interventional device moves beyond a threshold amount.

12. The workstation as recited in claim 9, further comprising:
a display configured to display the acquired images and a model image of the interventional device, wherein the image module, when executed by the processor, further generates the model image of the interventional device in accordance with the shape sensing information the model image indicating an updated position of the interventional device in the display without the imaging device acquiring another image.

13. The workstation as recited in claim 9, wherein the shape sensing module is optical fiber-based or electromagnetic.

14. The workstation as recited in claim 9, wherein the imaging device is guided by a scan prescription stored in the memory, the scan prescription being modified in accordance with the shape sensing information.

15. The workstation as recited in claim 9, wherein a radiation exposure frame rate of the imaging device is adjusted when it is determined that the images of the subject are to be acquired based upon the shape sensing information.

16. The workstation as recited in claim 9, further comprising:
a display configured to display the acquired images and a marker image, wherein the image module, when executed by the processor, further generates the marker image in accordance with the shape sensing information, the marker image indicating an updated position of the interventional device in the display without the imaging device acquiring another image.

17. A method of imaging a subject during a medical procedure, the method comprising:
shape sensing an interventional device to measure shape sensing information comprising shapes and locations of the interventional device in the subject;
determining when to acquire images by an imaging device based on an amount or type of movement of the interventional device indicated by to the shape sensing information;
generating automatically one or more control signals indicating when it is determined that images are to be acquired; and
adjusting the imaging device to acquire the images of the subject in response to the one or more control signals.

18. The method as recited in claim 17, wherein the imaging device includes an X-ray exposure device having an X-ray source.

19. The method as recited in claim 17, wherein it is determined to acquire the images when the interventional device moves beyond a threshold amount.

20. The method as recited in claim 19, further comprising generating a marker image in accordance with the shape sensing information to indicate an updated position of the interventional device in a display without the imaging device acquiring another image of the subject when the interventional device moves less than the threshold amount.

21. The method as recited in claim 17, further comprising generating a model image of the interventional device in accordance with the shape sensing information to indicate an updated position of the interventional device in a display without the imaging device acquiring another image of the subject.

22. The method as recited in claim 17, wherein the shape sensing is optical fiber-based or electromagnetic.

23. The method as recited in claim 17, wherein adjusting the imaging device includes guiding the imaging device by a scan prescription such that the scan prescription is modified in accordance with the shape sensing information.

24. The method as recited in claim 17, wherein adjusting the imaging device includes controlling a frame rate of the imaging device using the one or more control signals based upon the shape sensing information.

* * * * *